US005118823A

United States Patent [19]

Van Sickle et al.

[11] Patent Number: 5,118,823

[45] Date of Patent: Jun. 2, 1992

[54] OXIDATION OF DIHYDROXYAROMATIC COMPOUNDS TO QUINONES

[75] Inventors: Dale E. Van Sickle; Garry L. Myers; William D. Nottingham; Glenn C. Jones, all of Kingsport, Tenn.

[73] Assignee: Eastman Kodak Company, Rochester, N.Y.

[21] Appl. No.: 628,957

[22] Filed: Dec. 13, 1990

[51] Int. Cl.[5] .............................................. C07C 50/04

[52] U.S. Cl. ..................................... 552/293; 552/208

[58] Field of Search ................................ 552/293, 208

[56] References Cited

U.S. PATENT DOCUMENTS

| | | | |
|---|---|---|---|
| 3,213,114 | 10/1965 | Braxton et al. | 260/396 |
| 3,646,073 | 2/1972 | Wollensak | 260/396 |
| 3,670,034 | 6/1972 | Robinson | 552/293 |
| 4,208,339 | 6/1980 | Constantini et al. | 260/396 |
| 4,482,493 | 11/1984 | Matsumoto et al. | 552/293 |

FOREIGN PATENT DOCUMENTS 1478465 6/1977 United Kingdom .

OTHER PUBLICATIONS

*Organic Syntheses,* Collected vol. II, pp. 553–554, John Wiley and Sons, New York (1943).

*Organic Syntheses,* Collected Vol. I, pp. 482–484, John Wiley and Sons, New York (1941).

H. Firouzabadi et al., *Synthetic Communications,* 14, p. 875 (1984).

J. Skarzewski, *Tetrahedron,* 40, p. 4997 (1984).

M. Ignaczak et al., *Pol. J. Chem.,* 54, p. 259 (1980).

A. E. Gekhman et al., *Kinet. Katal.,* 30, No. 2, pp. 362–367 (1989).

J. P. Singh et al., *J. Indian Chem. Soc.,* 64, p. 440 (1987).

A. Aramata, *J. Electroanal. Chem., Interfacial Electrochem.,* 182, p. 197 (1985).

D. T. Chin et al., *J. Appl. Electrochem.,* 19, pp. 459–461 (1989).

R. J. Radel et al., *Ind. Eng. Chem. Prod. Res. Dev.,* 21, pp. 566–570 (1982).

J. Cason, *Organic Reactions,* 4, John Wiley and Sons, Inc., pp. 305–361 (1948).

*Primary Examiner*—C. Warren Ivy

*Assistant Examiner*—Raymond Covington

*Attorney, Agent, or Firm*—Thomas R. Savitsky; Betty J. Deaton; William P. Heath, Jr.

[57] ABSTRACT

Disclosed is a process for making quinones by oxidation of dihydroxyaromatic compounds in the presence of oxygen using supported platinum catalysts.

20 Claims, No Drawings

OXIDATION OF DIHYDROXYAROMATIC COMPOUNDS TO QUINONES

FIELD OF THE INVENTION

The present invention concerns a process for the oxidation of dihydroxyaromatic compounds to quinones using supported platinum catalysts.

BACKGROUND OF THE INVENTION p-Benzoquinone is a valuable chemical intermediate which is used in the preparation of herbicides, dyes, photographic initiators and the like. It is also useful as an inhibitor in processing certain vinyl monomers such as acrylic acid and as a dehydrogenation agent. Other quinones such as methyl-p-benzoquinone, cyclohexyl-p-benzoquinone, phenyl-p-benzoquinone, o-benzoquinone, 1,4-naphthoquinone and the like are also valuable chemical intermediates.

One classical method of making p-benzoquinone involves the oxidation of aniline using manganese dioxide catalyst in the presence of water and sulfuric acid. This process produces substantial quantities of inorganic solid by-products.

Another process is concerned with the oxidation of phenol using oxygen or an oxygen containing gas in the presence of cuprous or cupric ions and selected metals including nickel, iron, tin, cobalt, chromium, molybdenum and magnesium (U.S. Pat. No. 4,208,339).

Because of the ready availability of hydroquinone, it would also be desirable to provide efficient catalytic processes for converting it to p-benzoquinone.

Classical methods for converting hydroquinone to p-benzoquinone include oxidation of hydroquinone in the presence of sodium chlorate, vanadium pentoxide, and sulfuric acid [Organic Syntheses, Coll. Vol. II, p. 553, John Wiley and Sons, New York (1943)] and by means of oxidation using sodium dichromate in sulfuric acid solution [Organic Syntheses, Coll. Vol. I, p. 482, John Wiley and Sons, New York (1941)]. These processes produce corrosive by-products which damage processing equipment and they are not desirable from an environmental standpoint. Also p-benzoquinone reacts with water at an appreciable rate. Thus, a catalytic process which does not produce objectionable by-products and which can be operated in a nonaqueous system would be highly desirable.

Other prior art of interest includes U.S. Pat. No. 3,213,114 which describes a process for preparing a 2,6-dialkyl p-benzoquinone (but not uhsubstituted p-benzoquinone) which involves oxidation of a 2,4,6-tri-tert-alkylphenol with oxygen using an oxidation catalyst. Unsupported platinum is mentioned, but it is taught that only 2,4,6-tri-tert-alkylphenols can be employed in the process.

French Patent 1,338,462 describes the oxidation of hydroquinone to p-benzoquinone at 80° C. using oxygen in glacial acetic acid or propionic acid using 5% Ru or Rh supported on carbon. Also, in French Addition Patent 83,108 (1964) it is disclosed that water can be used as the solvent rather than acetic or propionic acid.

Finally, R. J. Radel et al., Ind. Eng. Chem. Prod. Res. Dev. 21, 566 (1982) reports on the use of Ru and Rh (but not Pt) for hydroquinone oxidation.

None of the prior art references teach the use of a supported platinum catalyst for preparation of quinones.

SUMMARY OF THE INVENTION

The present invention provides an economical and efficient process for making quinones in high purity and high yield from readily available raw materials.

More specifically, the present invention is directed to a process for the preparation of a quinone compound comprising contacting a dihydroxyaromatic compound with oxygen in the presence of a catalytic amount of a supported platinum catalyst and in a suitable solvent under conditions which promote formation of the desired quinone compound.

DETAILED DESCRIPTION OF THE INVENTION

The process of this invention involves the oxidation of dihydroxyaromatic compounds using supported platinum catalysts and oxygen as the oxidizing agent. The oxygen is preferably provided in a gaseous form such as pure gaseous oxygen, oxygen enriched air, or air. Carbon and alumina have been found to be effective supports for the platinum. Although the amount of platinum on the support may be varied, a concentration of about 5% has been found to be highly effective.

The oxidations are generally conducted in an anhydrous solvent such as acetic acid, propionic acid, butyric acid, isobutyric acid, octanoic acid, 2-ethylhexanoic acid and the like. Mixtures of these organic acids or organic acids containing various minor amounts of water are also operable as solvents. However, anhydrous solvents such as glacial acetic acid and anhydrous 2-ethylhexanoic acid are preferred.

These heterogeneous oxidation reactions may be conducted batchwise or in a continuous manner. It has been found that the catalyst can be readily recovered by a filtration procedure and recycled at least four times. In continuous operations, it is possible to use a static bed containing supported catalyst and the process stream is passed through this bed.

Dihydroxyaromatic compounds which are useful in this invention include hydroquinone, methylhydroquinone, dimethylhydroquinone, trimethylhydroquinone, cyclohexylhydroquinone, phenylhydroquinone, 1,2-dihydroxynaphthalene, 1,4-dihydroxynaphthalene, 2,6-dihydroxynaphthalene, and the like.

Preferred dihydroxyaromatic compounds are hydroquinone, cyclohexylhydroquinone, and phenylhydroquinone.

Reaction temperatures of about 40° C. to about 90° C. are useful in the process of this invention, but temperatures of about 70° C. to about 85° C. are preferred. In general, operating pressures of about 15 to about 150 psig partial oxygen pressure is more preferred.

Preferred supports for the supported platinum catalyst include carbon, alumina, and the like. The amount of supported platinum catalyst in the liquid reaction mixture is preferably about 0.2 to about 2.0 weight %, with about 0.5% being more preferred, said percentages being based on the total weight of the reaction mixture. The supported platinum catalyst preferably comprises about 1 to about 10 weight % platinum with about 5% being preferred. For the 5% platinum on carbon or 5% platinum on alumina catalysts, 10% quantities of catalyst, based on weight of the dihydroxyaromatic compound, provide for efficient conversion of the substrate to the desired quinone products. However, other concentrations of catalyst may be used if desired.

Concentrations of about 1 to about 15% dihydroxyaromatic compound in acetic acid or other suitable solvent may be used. Preferred concentrations are about 6 to about 12%, based on the total weight of the liquid reaction mixture.

The oxidation reactions generally proceed at a rapid rate and complete conversion of dihydroxyaromatic compound to quinone compound is achieved in about 100 to about 250 minutes at 80° C. using the above-described catalyst and substrate concentrations. Yields of quinone products are quite high in this process and generally fall in the 90–100% region, based on the theoretical maximum conversion of dihydroxyaromatic compound. The oxidation rates and yields of product obtained using the supported platinum catalyst are much higher than those obtained with prior art catalysts such as the rhodium on carbon and ruthenium on carbon catalysts cited in French Patent 1,338,462.

The following examples will further illustrate the invention.

EXAMPLE 1

A total of 1.0 g (0.009 mole) of hydroquinone dissolved in 20 mL of glacial acetic acid and 0.11 g of 5% platinum on carbon are placed in a 100 mL round bottom, heavy glass bulb with an inlet stem made of 8 mm o.d. capillary tubing. The stem is attached to the oxygen tank reservoir through flexible 1/16 inch o.d. stainless steel tubing using a 5/16 inch Swagelok fitting with nylon ferrule. The oxidation bulb is placed in an oil bath heated to 80° C. and agitated by means of a wrist-action shaker. The bulb is pressured to 65 psig with oxygen and the consumption of oxygen is followed by the pressure drop as read from a gauge attached to the oxygen reservoir. The oxidation is continued for 120 minutes and 4.52 millimoles of oxygen are used. The flask is cooled to 25° C. and the reaction mixture is filtered to remove catalyst. The catalyst is washed while on the filter with 10 mL of glacial acetic acid. Assay of the acetic acid solution shows 0.94 g (97% yield) of p-benzoquinone has been formed.

Similarly good results are achieved when cyclohexylhydroquinone is used instead of hydroquinone and cyclohexyl-1,4-benzoquinone is obtained in good yield.

EXAMPLE 2

A titanium autoclave is charged with 50 g hydroquinone, 450 g acetic acid and 10 g of 5% platinum on carbon catalyst which has been recovered by filtration from a previous oxidation. The mix is pressured to 700 psig with air, heated to 80° C., stirred and sparged with air for 4 hours at a flow rate of $\frac{1}{4}$ mole/hr. The product solution is filtered and the filtrate concentrated by distilling away 380 ml of acetic acid under vacuum. Water (170 ml) is added to the pot residue and the mix cooled to 10° C. The crystalline product is collected by filtration, washed with water and dried over calcium chloride desiccant to yield 45.6 g (92.9 % yield) of p-benzoquinone. The NMR spectrum indicates the material to be essentially 100% p-benzoquinone with no contamination by hydroquinone.

EXAMPLE 3

The procedure of Example 1 is repeated using 2.0 g (0.019 mole) of hydroquinone, 40 mL of glacial acetic acid, 0.14 g of 5% platinum on carbon, and 65 psig oxygen at 80° C. for 150 minutes. After filtering off the catalyst, the acetic acid solvent is distilled away to provide a 93% yield of p-benzoquinone.

EXAMPLE 4

The procedure of Example 1 is repeated using 0.13 g of 5% platinum on alumina catalyst, 1.02 g of hydroquinone, 20 ml of acetic acid and 65 psig oxygen at 80° C. After 180 minutes 4.75 millimoles of oxygen are absorbed. Filtration of the catalyst gives a solution which assays 52.5 mg/ml benzoquinone and zero hydroquinone for a conversion and yield of 100%.

EXAMPLE 5—Comparative Example

The procedure of Example 1 is repeated using 1.0 g (0.009 mole) of hydroquinone, 20 mL glacial acetic acid, 0.10 g of 5% rhodium on carbon and 65 psig oxygen at 80° C. for 240 minutes. The total millimoles of oxygen used is only 1.75. Assay of the reaction mixture by polarography shows substantial amounts of unreacted hydroquinone to be present and the yield of p-benzoquinone is only 16%.

EXAMPLE 6—Comparative Example

The procedure of Example 1 is repeated using 1.0 g (0.009 mole) of hydroquinone, 20 mL of glacial acetic acid, 0.11 g of 5% ruthenium on alumina and 65 psig oxygen at 80° C. for 180 minutes. The total millimoles of oxygen used is 1.39 and the yield of p-benzoquinone is only 9%.

EXAMPLE 7

The procedure of Example 1 is repeated using 8.0 g (0.073 mole) of hydroquinone, 60 mL of glacial acetic acid, 1.3 g of 5% platinum on carbon, and 65 psig oxygen at 80° C. for 124 minutes. The total millimoles of oxygen used is 40.2. The yield of p-benzoquinone is 100%.

EXAMPLE 8

The procedure of Example 1 is repeated using 2.2 g (0.02 mole) of hydroquinone, 20 g of 2-ethylhexanoic acid solvent, 0.32 g of 5% platinum on carbon catalyst and 50 psig oxygen at 80° C. for 300 minutes. The solution is filtered hot to remove catalyst residues. When the solution cools to 25° C., the p-benzoquinone crystallizes from the solvent. The crystals are filtered and dried to provide a 100% yield of p-benzoquinone, Tm 114° C.

The invention has been described in detail with particular reference to preferred embodiments thereof, but it will be understood that variations and modifications can be effected within the spirit and scope of the invention.

We claim:

1. A process for the preparation of a quinone compound comprising contacting a dihydroxyaromatic compound with oxygen in the presence of a catalytic amount of a supported platinum catalyst and in a suitable solvent under conditions which promote formation of the desired quinone compound.

2. The process of claim 1 wherein the catalytic amount of catalyst is about 0.2 to about 2 weight %, based on the total weight of the reaction mixture.

3. The process of claim 2 wherein the supported catalyst comprises about 1 to about 10 weight % of platinum.

4. The process of claim 3 wherein the support for the supported platinum catalyst is carbon or alumina.

5. The process of claim 1 wherein said suitable solvent is an anhydrous solvent selected from the group consisting of acetic acid, acetonitrile, propionic acid, butyric acid, isobutyric acid, octanoic acid, 2-ethylhexanoic acid, and a mixture thereof; or a mixture of one or more of said acids with a minor amount of water.

6. The process of claim 1 wherein said suitable solvent is glacial acetic acid or anhydrous 2-ethylhexanoic acid.

7. The process of claim 1 wherein said dihydroxyaromatic compound is selected from the group consisting of hydroquinone, methylhydroquinone, dimethylhydroquinone, trimethylhydroquinone, cyclohexylhydroquinone, phenylhydroquinone, 1,2-dihydroxynaphthalene, 1,4-dihydroxynaphthalene, and 2,6-dihydroxynaphthalene.

8. The process of claim 1 wherein said dihydroxyaromatic compound is selected from the group consisting of hydroquinone, cyclohexylhydroquinone, and phenylhydroquinone.

9. The process of claim 1 wherein the concentration of dihydroxyaromatic compound is about 1 to about 15 weight %, based on the total weight of the reaction mixture.

10. The process of claim 1 wherein the concentration of dihydroxyaromatic compound is about 6 to about 12 weight %, based on the total weight of the reaction mixture.

11. The process of claim 1 wherein said oxygen is gaseous and is in the form of air, oxygen enriched air, or substantially pure oxygen.

12. The process of claim 1 carried out at a temperature of about 40° C. to about 90° C. at superatmospheric pressure.

13. The process of claim 1 carried out at a temperature of about 70° C. to about 85° C. at partial pressures of oxygen from about 15 to about 150 psig.

14. The process of claim 1 carried out at a reaction time of about 100 to about 250 minutes.

15. The process of claim 1 wherein the yield of quinone compound is about 90 to about 100% of the theoretical maximum conversion of dihydroxyaromatic compound.

16. The process of claim 1 carried out batchwise.

17. The process of claim 1 carried out continuously wherein the supported catalyst is recycled.

18. The process of claim 17 using a static bed containing the supported catalyst.

19. A process for the preparation of p-benzoquinone comprising contacting hydroquinone at a concentration of about 1 to about 15 weight %, based on the total weight of the reaction mixture, with gaseous oxygen or air in the presence of a catalytic amount of a supported catalyst which is platinum supported on carbon or platinum supported on alumina in an anhydrous carboxylic acid solvent at a temperature of about 40° C. to about 90° C. and at a partial pressure of oxygen of about 15 to about 150 psig.

20. The process of claim 19 wherein said anhydrous carboxylic acid solvent is glacial acetic acid; said temperature is about 70° C. to about 85° C.; the concentration of hydroquinone is about 6 to about 12 weight %, and the amount of supported catalyst is about 0.5 weight %, said percentages being based on the total weight of the reaction mixture; the supported catalyst consists essentially of about 5 weight % platinum and about 95 weight % carbon or alumina; said process is carried out for a reaction time of about 100 to about 250 minutes; and the yield of p-benzoquinone is about 90 to about 100%, based on the theoretical maximum conversion of hydroquinone.

* * * * *